United States Patent
Kimura

(10) Patent No.: US 8,283,640 B2
(45) Date of Patent: Oct. 9, 2012

(54) FLUORESCENCE DETECTION METHOD

(75) Inventor: Muneyasu Kimura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 392 days.

(21) Appl. No.: 12/680,106

(22) PCT Filed: Sep. 24, 2008

(86) PCT No.: PCT/JP2008/002642
§ 371 (c)(1),
(2), (4) Date: Mar. 25, 2010

(87) PCT Pub. No.: WO2009/041032
PCT Pub. Date: Apr. 2, 2009

(65) Prior Publication Data
US 2010/0258740 A1    Oct. 14, 2010

(30) Foreign Application Priority Data
Sep. 28, 2007  (JP) .................... 2007-255403

(51) Int. Cl.
*G01J 1/58* (2006.01)

(52) U.S. Cl. .................................... 250/459.1
(58) Field of Classification Search ........... 250/459.1
See application file for complete search history.

(56) References Cited

U.S. PATENT DOCUMENTS
7,235,357 B2    6/2007  Iwaki et al.
2007/0002325 A1  1/2007  Tabata et al.

FOREIGN PATENT DOCUMENTS
| JP | 2002-181708 A | 6/2002 |
| JP | 2003-084002 A | 3/2003 |
| JP | 2006-226803 A | 8/2006 |
| JP | 2007-278984 A | 10/2007 |
| JP | 2008-122297 A | 5/2008 |

*Primary Examiner* — David Porta
*Assistant Examiner* — Hugh H Maupin
(74) *Attorney, Agent, or Firm* — Sughrue Mion, PLLC

(57) ABSTRACT

A fluorescence detection method allows fluorescence intensity detection from a fluorescently-labeled biological sample with high accuracy in shorter time, even when a fluorescence intensity from a microchip itself acting as background. A fluorescence intensity from an equivalent microchip, which is equivalent to a microchip with the fluorescently-labeled biological sample, is detected for a period from the start of application of excitation light until the intensity sufficiently attenuates, and a temporal change of the intensity is stored. The light is applied to the microchip and the sample is fed before the fluorescence intensity from the microchip sufficiently attenuates to detect the fluorescence intensity for a period from the start of application of the light to a point after the sample is fed. Values of the temporal change are subtracted from the intensity detected from the microchip with the sample to detect an intensity of fluorescence emitted from the sample.

8 Claims, 7 Drawing Sheets

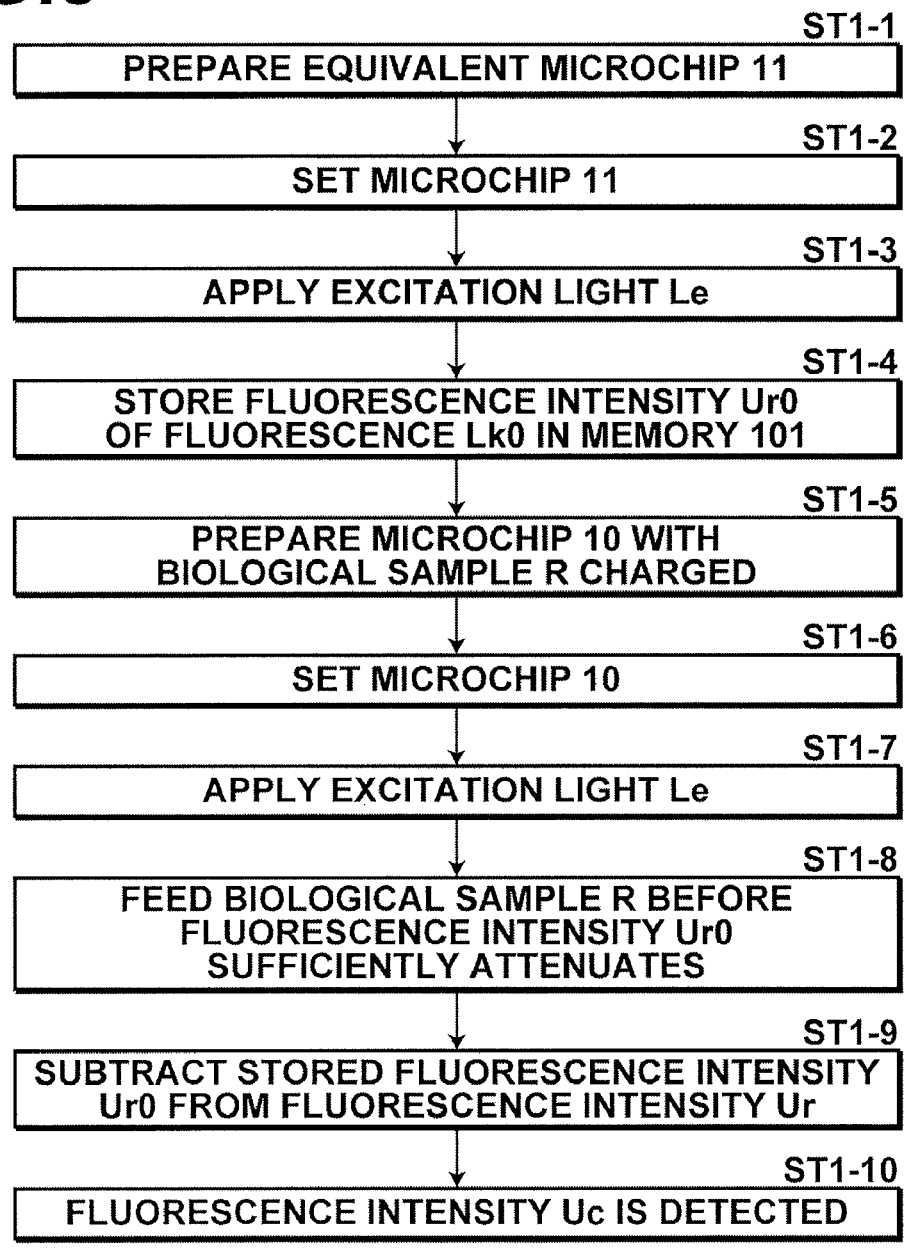

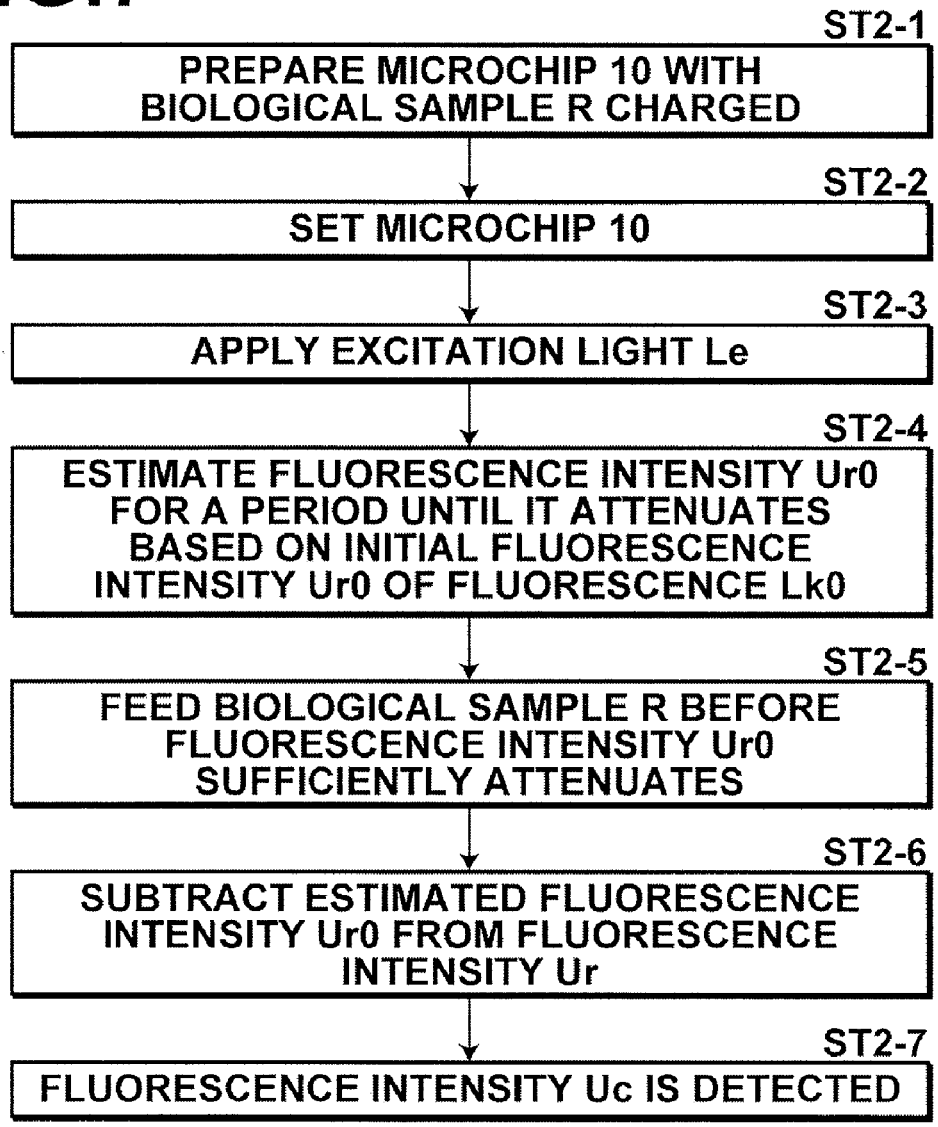

FLUORESCENCE DETECTION METHOD

TECHNICAL FIELD

The present invention relates to a fluorescence detection method in which a fluorescently-labeled biological sample is fed to a microchip and excitation light is applied thereto to detect an intensity of emitted fluorescence.

BACKGROUND ART

Fluorescence detection methods for detecting an intensity of fluorescence which is emitted from a fluorescently-labeled biological sample have conventionally been known. According to the fluorescence detection methods, separation or identification of a gene sequence, a level of gene expression, or a protein, or evaluation of a molecular weight or a property can be achieved by detecting the fluorescence intensity.

For example, μTAS-immunoassay system (Micro Total Analysis System—Enzyme Linked Immuno-Sorbent Assey (ELISA) has been known. This uses a microchip which is provided with a micro flow channel having very small width and depth. An electrophoretic fluid (buffer fluid) is injected into the flow channel of the microchip, and a biological sample is injected into the micro flow channel. Then, a high voltage (electrophoretic voltage) is applied to induce electrophoresis, and an obtained substance is exposed to excitation light at a measurement area of the microchip to excite the fluorescent label. Then, the intensity of the thus emitted fluorescence is detected to analyze the substance derived from a living organism.

A further example of a microchip-based analysis device is a microarray, and a microarray analysis system has attracted attention. For example, a specific binding substance which can bind specifically to a substance derived from a living organism, such as a hormone, a tumor marker, an enzyme, an antibody, an antigen, an abzyme, any of other kind of proteins, a nucleic acid, a cDNA, a DNA or a RNA, and which has a known base sequence, a known base length, a known composition, and the like, is dropped, using a spotter device, at different positions on a surface of a carrier, such as a slide glass plate or a membrane filter, of the microarray to form a number of independent spots. Then, a fluorescently-labeled substance, which is a substance collected from a living organism through extraction, isolation, or the like, or derived from a living organism and subjected to a chemical treatment or chemical modification, such as a hormone, a tumor marker, an enzyme, an antibody, an antigen, an abzyme, any of other proteins, a nucleic acid, a cDNA, a DNA or a mRNA, is bound specifically to the specific bonding substance on the microarray through hybridization, or the like. Then, excitation light is applied to the microarray, and the intensity of fluorescence emitted from the fluorescent label is photoelectrically detected to analyze the substance derived from a living organism.

In the above-described analysis technique, however, the fluorescence emitted from the fluorescently-labeled biological sample fed to the microchip when it is exposed to the excitation light includes not only the fluorescence emitted from the fluorescently-labeled biological sample but also fluorescence emitted from the microchip itself. The fluorescence emitted from the microchip acts as background and lowers the accuracy, i.e., the S/N ratio, of the detection of the fluorescence intensity.

In a fluorescence detection method proposed in Japanese Unexamined Patent Publication No. 2002-181708, the fluorescence emitted from the fluorescently-labeled biological sample is detected after the intensity of the fluorescence emitted from the microchip itself has sufficiently attenuated. In this method, even if the fluorescence emitted from the microchip itself acts as the background, its intensity is small. Thus, influence of the fluorescence emitted from the microchip itself is reduced, thereby minimizing lowering of the accuracy of detection, i.e., the S/N ratio.

In a method proposed in Japanese Unexamined Patent Publication No. 2003-084002, the background is reduced by treating the microchip with a blocking agent containing a quencher.

In recent years, however, in order to reduce the cost of the microchip, use of a resin material, in place of conventional silica glass, has been proposed as a material forming the microchip. When the excitation light is applied to a resin microchip, the detected fluorescence emitted from the microchip itself is more intense than that from a silica glass microchip. Since the resin microchips are thicker than the silica glass microchips to ensure flatness after the shape forming thereof, more intense fluorescence is emitted therefrom. Therefore, it takes longer time for the intensity of the fluorescence emitted from the microchip itself to sufficiently attenuate than that from the conventional silica glass microchip, and therefore the fluorescence emitted from the microchip acts as the background for longer time. Thus, the influence thereof exerted on the accuracy of detection of the fluorescence intensity of the biological sample is higher. Further, in order to improve productivity of fluorescence detection apparatuses, there is a demand for reduction of time taken for detecting the intensity of the fluorescence emitted from the fluorescently-labeled biological sample.

In the technique disclosed in Japanese Unexamined Patent Publication No. 2002-181708, although the influence of the fluorescence emitted from the microchip itself acting as the background on the accuracy of detection of the fluorescence intensity can be reduced, a time taken for detecting the fluorescence intensity from the biological sample cannot be reduced.

In the technique disclosed in Japanese Unexamined Patent Publication No. 2003-084002, it is necessary to treat the microchip with the blocking agent containing a quencher, and this increases the cost of the microchip.

DISCLOSURE OF INVENTION

In view of the above-described circumstances, the present invention is directed to providing a fluorescence detection method which allows detection of the fluorescence intensity from a fluorescently-labeled biological sample with high accuracy and in a shorter time without necessitating an additional treatment on the microchip, even if the intensity of the fluorescence emitted from the microchip itself acts as the background.

In order to solve the above-described problem, the fluorescence detection method of the invention is a fluorescence detection method for detecting a fluorescence intensity of fluorescence emitted when excitation light is applied to a microchip with a fluorescently-labeled biological sample fed thereto, the method including: detecting a fluorescence intensity of fluorescence emitted from an equivalent microchip itself for a period from the start of application of the excitation light until the fluorescence intensity sufficiently attenuates, the equivalent microchip being equivalent to the microchip; storing a temporal change of the detected fluorescence intensity; applying the excitation light to the microchip and feeding the biological sample to the microchip before a fluorescence intensity of fluorescence emitted from the microchip itself sufficiently attenuates; detecting the fluorescence intensity of the fluorescence emitted from the microchip for a period from the start of application of the excitation light to a point of time after the biological sample is fed to the microchip; and subtracting, from the fluorescence intensity detected from the microchip with the biological sample fed thereto, values of the stored temporal change of the fluorescence intensity of the fluorescence emitted from the equivalent microchip itself until the fluorescence intensity sufficiently attenuates, whereby detecting a fluorescence intensity of the fluorescence emitted from the biological sample exposed to the excitation light.

The term "feed" herein widely refers to moving the biological sample in the microchip to a position to be exposed to the excitation light. Specific examples thereof include electrophoresing the biological sample within the microchip provided with a micro flow channel to move the biological sample to a point within the micro flow channel to be exposed to the excitation light, or to move a specimen holding section of a microarray which is not provided with a micro flow channel to a position to be exposed to the excitation light. The "equivalent microchip" herein means a microchip that has the same shape, is made of the same material, or is made in the same production lot as the microchip to be used, and is preferably the same as the microchip to be used in all these respects. The "start of application of the excitation light" herein refers not only to a case where the detection is started immediately after the start of application of the excitation light, but also to a case where the detection is started some time after the start of application of the excitation light. The description "the fluorescence intensity sufficiently attenuates" refers to a state where the fluorescence intensity has attenuated to about 20%, or desirably to about 10%, of the value of the fluorescence intensity from the microchip itself detected at the start of application of the excitation light. The "temporal change of the fluorescence intensity" refers to temporal characteristics of the change of the detected fluorescence intensity induced by application of the excitation light. The description "before the fluorescence intensity sufficiently attenuates" refers to a point before the fluorescence intensity has attenuate to about 80%, or desirably to about 70%, of the value of the fluorescence intensity from the microchip itself detected at the start of application of the excitation light. The "point of time after the biological sample is fed" refers to a point of time after the fluorescence intensity of the fluorescence emitted from the fluorescently-labeled biological sample, which has been fed to the microchip and exposed to the excitation light, has sufficiently been detected, and not refers to a point of time immediately after the fluorescently-labeled biological sample is fed to the microchip.

In this fluorescence detection method, the steps of storing the temporal change of the fluorescence intensity of the fluorescence emitted from the equivalent microchip itself, which is equivalent to the microchip, may be carried out for each of more than one microchips made of different materials to store different types of temporal changes, and the subtraction may be carried out with selecting one of the different types of temporal changes to be used for the subtraction based on a material forming the microchip being used.

The "more than one microchips made of different materials" herein refers to that more than one microchips made of different materials are present. The "different types of temporal changes" refers to the temporal change for each of the more than one microchips made of different materials.

The description "based on a material forming the microchip being used" refers to determining from the material forming the microchip being used.

The fluorescence detection method according to a second aspect of the invention is a fluorescence detection method for detecting a fluorescence intensity of fluorescence emitted when excitation light is applied to a microchip with a fluorescently-labeled biological sample fed thereto, the method including: applying the excitation light to the microchip and feeding the biological sample to the microchip before a fluorescence intensity of fluorescence emitted from the microchip itself sufficiently attenuates; detecting the fluorescence intensity of the fluorescence emitted from the microchip for a period from the start of application of the excitation light to a point of time after the biological sample is fed to the microchip; estimating a temporal change of the fluorescence intensity of the fluorescence emitted from the microchip for a period until the fluorescence intensity sufficiently attenuates, based on an initial temporal change of the fluorescence intensity of the fluorescence emitted from the microchip obtained through the detection; and subtracting, from the fluorescence intensity detected from the microchip with the biological sample fed thereto, values of the estimated temporal change of the fluorescence intensity of the fluorescence emitted from the microchip for the period until the fluorescence intensity sufficiently attenuates, whereby detecting a fluorescence intensity of the fluorescence emitted from the biological sample exposed to the excitation light.

The description "based on an initial temporal change of the fluorescence intensity" herein refers to being based on a temporal change of the fluorescence intensity for a period after the start of application of the excitation light and before the biological sample is fed during which the fluorescence intensity attenuates to about 70%, or desirably to about 60%, of the value of the fluorescence intensity detected at the start of application of the excitation light. The "estimating a temporal change" herein refers to estimating values of the fluorescence intensity for a period until the fluorescence intensity sufficiently attenuates based on values of the initial temporal change of the fluorescence intensity.

The estimation of the temporal change may be carried out by approximation by an exponential function based on the initial temporal change of the fluorescence intensity of the fluorescence emitted from the microchip.

Alternatively, the estimation of the temporal change may be carried out by approximation by a power series based on the initial temporal change of the fluorescence intensity of the fluorescence emitted from the microchip.

Further alternatively, the estimation of the temporal change may be carried out by approximation by a logarithmic function based on the initial temporal change of the fluorescence intensity of the fluorescence emitted from the microchip.

Yet alternatively, the estimation of the temporal change may be carried out by approximation by a fractional function based on the initial temporal change of the fluorescence intensity of the fluorescence emitted from the microchip.

Still alternatively, the estimation of the temporal change may be carried out by selecting one of different types of temporal changes, which are obtained by detecting a fluorescence intensity of fluorescence emitted from each of different types of microchips exposed to the excitation light for a period from the start of application of the excitation light until the fluorescence intensity sufficiently attenuates, based on the initial temporal change of the fluorescence intensity of the fluorescence emitted from the microchip.

The "different types of microchips" herein include microchips that are made of the same material as the microchip to be used and are made in different production lots.

EFFECT OF INVENTION

According to the fluorescence detection method of the invention, the temporal change of the intensity of the fluorescence emitted from the microchip itself for the period until the fluorescence intensity sufficiently attenuates is stored in advance or the fluorescence intensity for the period until the fluorescence intensity sufficiently attenuates is estimated from the initial temporal change of the fluorescence intensity of the detected fluorescence, and values of the temporal change stored in advance or the estimated temporal change are subtracted from the fluorescence intensity detected from the microchip with the biological sample fed thereto. Therefore, the fluorescently-labeled biological sample can be fed without waiting until the fluorescence intensity of the fluorescence emitted from the microchip itself sufficiently attenuates, and the intensity of the fluorescence emitted from the fluorescently-labeled biological sample with reduced influence of the fluorescence emitted from the microchip itself acting as background can be detected. Further, a time taken for detecting the fluorescence intensity can be reduced. Moreover, it is not necessary to treat the microchip with a blocking agent containing a quencher and therefore the cost of the microchip is not increased.

BRIEF DESCRIPTION OF THE DRAWINGS

FIG. 5 is a flow chart according to a first embodiment of the invention, FIG. 7 is a flow chart according to a second embodiment of the invention.

DESCRIPTION OF PREFERRED EMBODIMENTS

Hereinafter, embodiments of the fluorescence intensity detection method of the present invention will be described with reference to the drawings.

Figure 1:
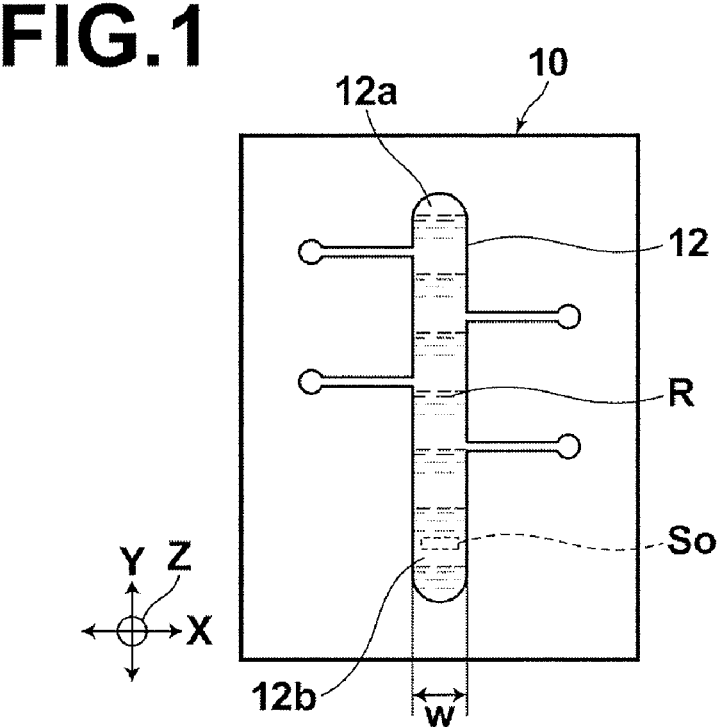
FIG. 1 is a diagram illustrating the schematic configuration of a microchip used for implementing the present invention.

FIG. 1 illustrates the schematic configuration of a microchip which is used for implementing the invention.

A microchip 10 includes a micro flow channel 12 which is formed by a channel having a width of about 100 µm (X-direction in the drawing) and a depth of about 24 µm (Z-direction in the drawing) extending in one direction (direction of arrow Y in the drawing). The material forming the microchip 10 is a resin material or silica glass. Specific examples of the resin material include PMMA (methyl methacrylate resin) and styrol resins. The micro flow channel 12 is capable to contain a fluorescently-labeled biological sample R.

Figure 2:
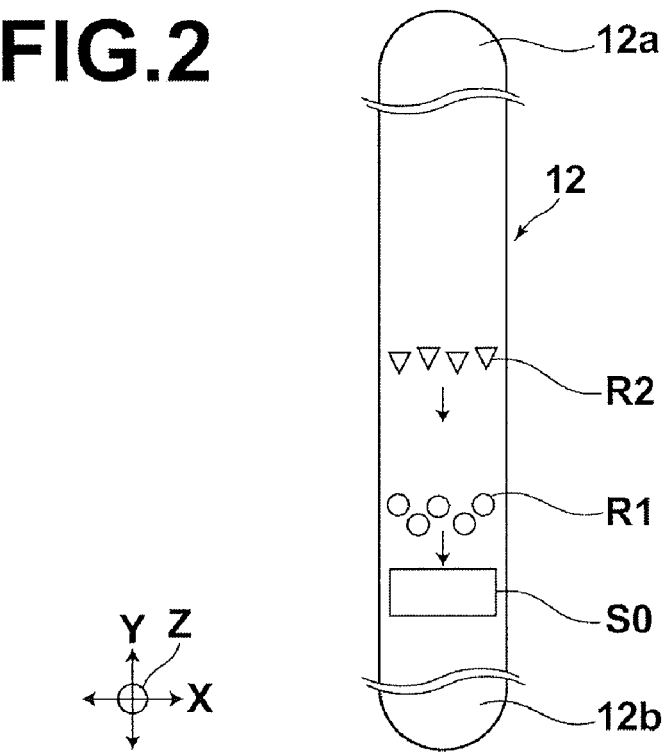
FIG. 2 is a schematic diagram illustrating a biological sample R being electrophoresed within a micro flow channel 12.

FIG. 2 is a schematic diagram illustrating the biological sample R which is electrophoresed within the micro flow channel 12.

Electrodes are inserted at one end portion 12a and the other end portion 12b of the micro flow channel 12 containing the biological sample R to provide a potential difference therebetween. In this embodiment, a potential difference of 3000 V, for example, is provided. By providing the potential difference, different components contained in the biological sample R move at different rates within the micro flow channel 12 along the length direction of the flow channel (direction of arrow Y in the drawing). That is, the different components are attracted to the electrode with different forces, so that the different components move at different rates within the micro flow channel 12 along the length direction of the flow channel. For example, a component R1 and a component R2 move within the micro flow channel 12 toward the end portion 12b. As described above, since the components R1 and R2 move at different rates, they are separately fed to an exposure area So in the micro flow channel 12, to which excitation light Le is applied from a confocal microscope 200, which will be described later.

Figure 3:
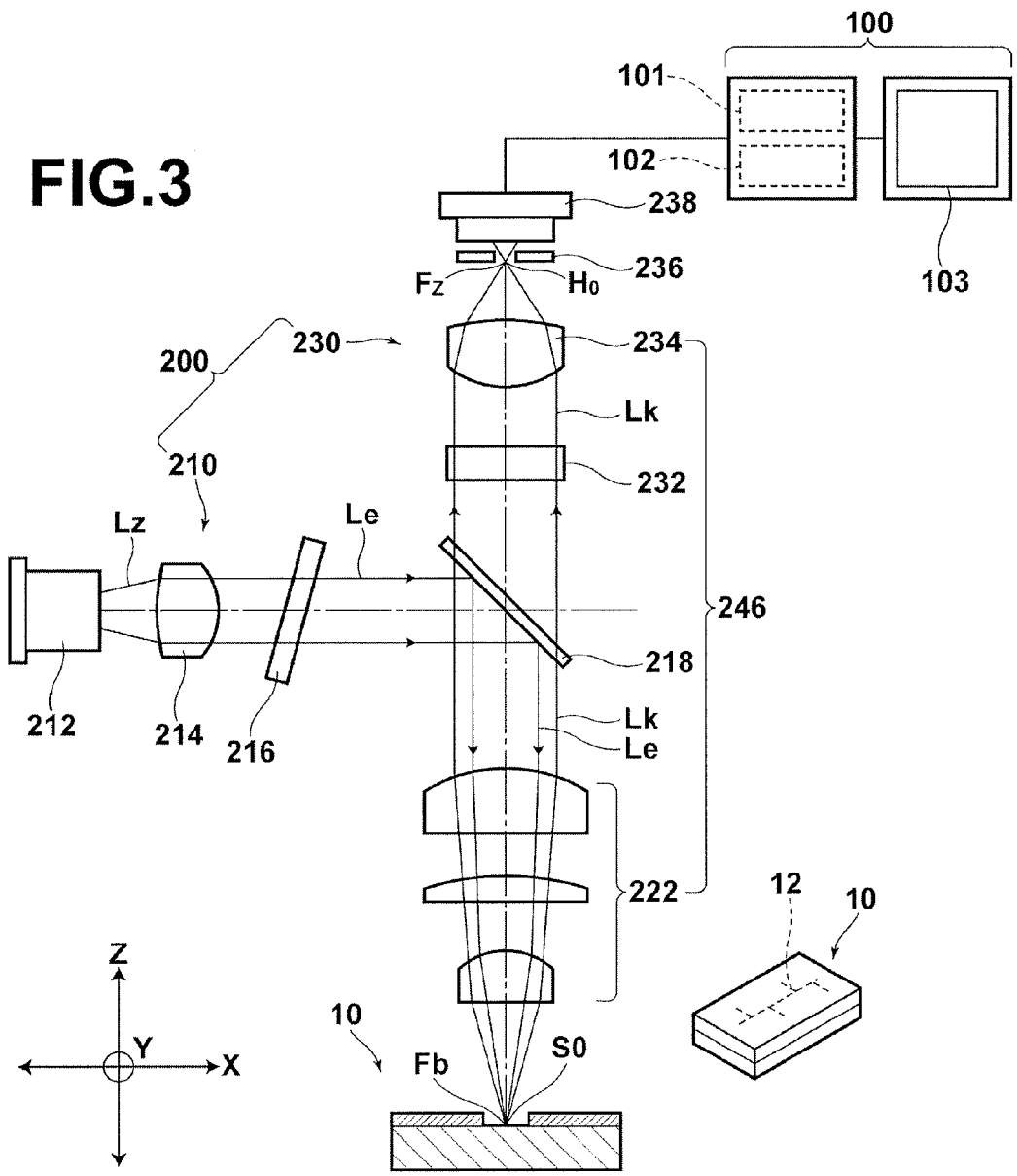
FIG. 3 is a diagram illustrating the schematic configuration of a confocal fluorescence microscope 200 and a controlling section 100 used for implementing the invention.

FIG. 3 illustrates the schematic configuration of a confocal fluorescence microscope 200 and a controlling section 100 which are used for implementing the invention.

The confocal fluorescence microscope 200 is used to identify the components contained in the biological sample R, and includes an excitation light applying section 210 to apply the excitation light Le and a fluorescence detection section 230 to detect a fluorescence intensity Ur of fluorescence Lk which is emitted when the excitation light Le is applied.

The controlling section 100 carries out processing to remove the influence of fluorescence Lk0, which is emitted from the microchip 10 itself and acts as the background, from the fluorescence intensity Ur detected by the confocal fluorescence microscope 200, and includes a memory 101 to store values of a temporal change of the fluorescence intensity Ur detected by the fluorescence detection section 230, a CPU 102 to calculate fluorescence intensity Uc with reduced influence of the background from the detected fluorescence intensity Ur, and a monitor 103 that can display both the detected fluorescence intensity Ur and the fluorescence intensity Uc with reduced influence of the background. The memory 101 can store values of temporal changes of more than one detected fluorescence intensities Ur.

Now, the configuration of the confocal fluorescence microscope 200 is described in detail. The excitation light applying section 210 applies the excitation light Le to a substance to be detected, and includes: a laser light source 212 to emit laser light Lz; a collimator lens 214 to collimate the emitted laser light Lz; a wavelength filter 216 to block unnecessary wavelength components in the laser light Lz and transmit light components within the wavelength range of the excitation light Le; a dichroic mirror 218 to reflect the transmitted excitation light Le; and an object point-side collecting lens 222 to collect the reflected excitation light Le onto an object point-side focal point Fb. Specifically, the excitation light Le used in this embodiment is red laser light having a wavelength of about 640 nm and an output power of about 10 mW. The dichroic mirror 218 reflects the excitation light Le and transmits the fluorescence Lk. It should be noted that the excitation light applying section 210 and the fluorescence detection section 230 share the same dichroic mirror 218 and object point-side collecting lens 222.

The fluorescence detection section 230 detects the fluorescence Lk emitted from the substance to be detected when it is exposed to the excitation light Le, and includes: an object point-side collecting lens 222 to collect the fluorescence Lk emitted from the substance to be detected; a dichroic mirror 218 to transmit the fluorescence Lk outputted from the object point-side collecting lens 222 and reflect the excitation light Le; a noise light cut filter 232 to block noise light which is mixed in the transmitted fluorescence Lk; a pinhole plate 236 having a pinhole Ho formed therein; an image point-side collecting lens 234 to collect the fluorescence Lk, which has passed through the noise light cut filter 232, into the pinhole Ho formed in the pinhole plate 236; and a detector unit 238 to detect the fluorescence Lk, which has passed through the pinhole Ho. Specifically, in this embodiment, the fluorescence intensity Ur of the fluorescence Lk having a wavelength of about 677 nm is detected. The object point-side collecting lens 222 and the image point-side collecting lens 234 form an imaging optical system 246 for focusing an image of a point on the substance to be detected into the pinhole Ho. A point on the substance to be detected positioned at the object point-side focal point Fb and the pinhole Ho positioned at an image point-side focal point Fz are in a conjugate positional relationship relative to the imaging optical system 246.

Next, an operation of identifying the components contained in the biological sample R in the micro flow channel 12 using the confocal fluorescence microscope 200 is described.

The microchip 10 is set on the confocal fluorescence microscope 200. At this time, the object point-side focal point Fb of the confocal fluorescence microscope 200 is positioned at the exposure area So in the micro flow channel 12 of the microchip 10.

The excitation light Le is applied from the excitation light applying section 210 to the exposure area So. The fluorescence Lk emitted from the exposure area So in the micro flow channel 12, which is exposed to the excitation light Le, is directed to the fluorescence detection section 230.

The fluorescence detection section 230 focuses the incoming fluorescence Lk into the pinhole Ho, and the fluorescence Lk passed through the pinhole Ho is detected by the detector unit 238. Here, the shape of the image of the fluorescence Lk focused into the pinhole Ho conforms to the shape of the exposure area So. It should be noted that, in the confocal fluorescence microscope 200, since the exposure area So in the micro flow channel 12 positioned at the object point-side focal point Fb and the pinhole Ho positioned at the image point-side focal point Fz are in the conjugate positional relationship, fluorescence emitted from positions other than the exposure area So when the excitation light Le is applied, the excitation light, and the like, are blocked at the pinhole Ho and are scarcely detected by the detector unit 238.

By electrophoresing the biological sample R, as shown in FIG. 2, the component R1 and the component R2, for example, move within the micro flow channel 12 toward the end portion 12b. Since the components R1 and R2 move at different rates, they are fed to the exposure area So in turn. As the components R1 and R2 are fed to the exposure area So, fluorescence rays Lk1 and Lk2 are emitted in turn from the components R1 and R2.

Returning to FIG. 3, the fluorescence Lk emitted from the biological sample R is detected at the fluorescence detection section 230. For example, the fluorescence rays Lk1 and Lk2 emitted from the components R1 and R2 are detected in turn as fluorescence intensities Ur1 and Ur2. The detected fluorescence intensity Ur is stored in the memory 101 of the controlling section 100 over time, so that times T1 and T2 taken for the components R1 and R2 passing through the exposure area So, for example, can be obtained.

In this manner, by comparing the fluorescence intensities Ur1 and Ur2 or by comparing the times T1 and T2 taken for the components R1 and R2 to be fed to the exposure area So, for example, the components contained in the biological sample R can be identified. Specifically, if the component R1 is a known component, the component R2 can relatively be identified by dividing the fluorescence intensity Ur1 by the fluorescence intensity Ur2 with using the component R1 as a reference.

It should be noted that individual components may be identified by providing the microchip 10 with more than one micro flow channels 12 and letting different components flow through different flow channels.

Next, temporal change of the detected fluorescence intensity Ur is described.

Figure 4A:
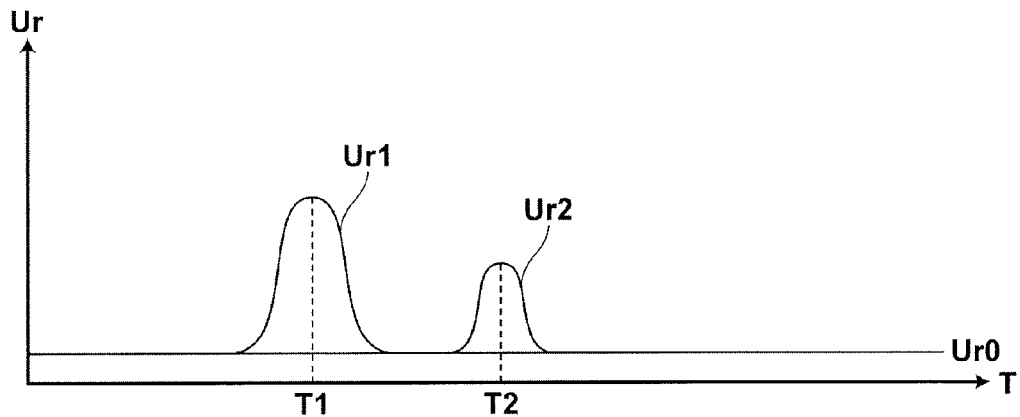
FIG. 4A shows an ideal temporal change of a fluorescence intensity Ur.
Figure 4B:
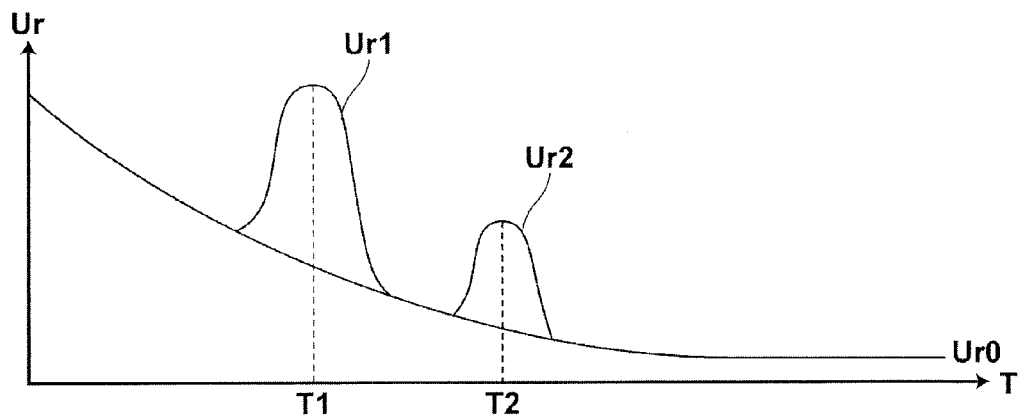
FIG. 4B shows an actual temporal change of the fluorescence intensity Ur.
Figure 4C:
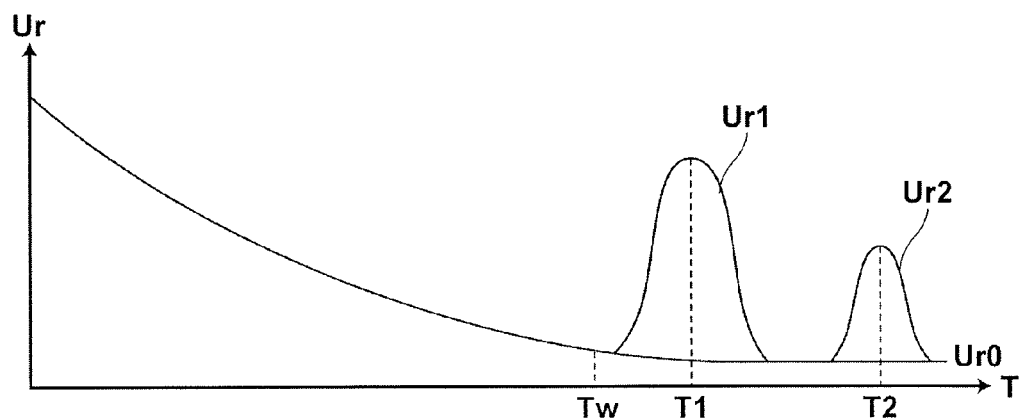
FIG. 4C shows a temporal change of the fluorescence intensity Ur in prior art.

FIGS. 4A to 4C show temporal changes of the detected fluorescence intensity Ur. In FIGS. 4A to 4C, the abscissa axis represents time T and the ordinate axis represents the fluorescence intensity Ur.

FIG. 4A shows an ideal temporal change of the fluorescence intensity Ur. Since no fluorescence is emitted from the microchip 10 itself, the fluorescence Lk is emitted only from the biological sample R being electrophoresed. For example, the fluorescence intensities Ur1 and Ur2 of the fluorescence rays Lk1 and Lk2 emitted from the components R1 and R2 in the biological sample R are detected in turn at detection times T1 and T2 without addition of a fluorescence intensity Ur0 of fluorescence Lk0 emitted from the microchip 10 itself. Therefore, the components R1 and R2 can be identified with high accuracy based on the detected fluorescence intensities Ur1 and Ur2.

FIG. 4B shows an actual temporal change of the fluorescence intensity Ur. Since the fluorescence Lk0 is emitted from the microchip 10 itself, the fluorescence intensity Ur0 is detected. The fluorescence intensity Ur0 acts as the background and to be added to the fluorescence intensity Ur. For example, the fluorescence intensities Ur1 and Ur2 of the components R1 and R2 in the biological sample R are detected at the detection times T1 and T2 with being added to the fluorescence intensity Ur0 from the microchip 10 itself.

FIG. 4C shows a temporal change of the fluorescence intensity Ur in prior art. In the prior art, in order to reduce the influence of the fluorescence intensity Ur0 from the microchip 10 itself as the background, a predetermined waiting time Tw is provided so that the components R1 and R2, for example, in the biological sample R are fed to the exposure area So after the fluorescence intensity Ur0 has sufficiently attenuated, to detect the fluorescence intensities Ur1 and Ur2 from the components R1 and R2 at the detection times T1 and T2. Specifically, in a case where the microchip made of PMMA is used in this embodiment, a waiting time Tw of about 300 seconds from the start of application of the excitation light is provided.

Now, the fluorescence detection method of the invention is described.

FIG. 5 is a flow chart according to a first embodiment of the invention.

A microchip 11, which has no fluorescently-labeled biological sample R charged in the micro flow channel 12 thereof and which is equivalent to the microchip 10 to be used later for identifying the components in the biological sample R, is prepared (ST1-1). It should be noted that the number of the equivalent microchip 11 is not limited to one, and more than one equivalent microchips 11 made of different materials may be prepared.

The equivalent microchip 11 is set on the confocal fluorescence microscope 200 to be ready for detecting the fluorescence intensity Ur (ST1-2).

The excitation light Le is applied to the equivalent microchip 11, and the fluorescence intensity Ur0 of the fluorescence Lk0 emitted from the equivalent microchip 11 itself exposed to the excitation light Le is detected (ST1-3).

The detection is continued until the fluorescence intensity Ur0 sufficiently attenuates, and the temporal change of the fluorescence intensity Ur0 is stored in the memory 101 of the controlling section 100 (ST1-4). Specifically, in a case where the microchip made of PMMA is used in this embodiment, it is about 200 seconds from the start of application of the excitation light Le during which the fluorescence intensity Ur0 attenuates to about 20%, or preferably about 300 seconds from the start of application of the excitation light Le during which the fluorescence intensity Ur0 attenuates to about 10%. It should be noted that, in a case where more than one equivalent microchips 11 made of different materials are prepared, the fluorescence intensity Ur0 is stored for each equivalent microchip 11.

The microchip 10 with the fluorescently-labeled biological sample R charged in the micro flow channel 12 thereof is prepared (ST1-5).

The microchip 10 is set on the confocal fluorescence microscope 200 to be ready for detecting the fluorescence intensity Ur (ST1-6).

The excitation light Le is applied to the microchip 10 with the fluorescently-labeled biological sample R charged in the micro flow channel 12 thereof, and the fluorescence intensity Ur0 of the fluorescence Lk0 emitted from the microchip 10 itself exposed to the excitation light Le is detected (ST1-7).

Before the fluorescence intensity of the fluorescence intensity Ur0 sufficiently attenuates, the biological sample R is electrophoresed to be fed to the exposure area So (ST1-8). For example, the components R1 and R2 are fed to the exposure area So. Specifically, in a case where the microchip made of PMMA is used, feed timing is about 20 seconds from the start of application of the excitation light Le during which the fluorescence intensity Ur0 attenuates to about 80%, or desirably about 40 seconds from the start of application of the excitation light Le during which the fluorescence intensity Ur0 attenuates to about 70%.

Values of the temporal change of the fluorescence intensity Ur0 from the equivalent microchip 11 stored in the memory 101 of the controlling section 100 are read out, and the temporal change of the stored fluorescence intensity Ur0 is subtracted from the temporal change of the detected fluorescence intensity Ur (ST1-9). It should be noted that, in a case where values of temporal changes for more than one equivalent microchips 11 made of different materials are stored, values of the temporal change for one of the equivalent microchips 11 which is made of the same material as the microchip 10 used for identifying the components in the biological sample R may be selected and read out from the memory 101.

The fluorescence intensity Uc with reduced influence of the fluorescence intensity Ur0 as the background is detected (ST1-10). For example, fluorescence intensities Uc1 and Uc2 of the components R1 and R2 are detected.

Figure 6A:
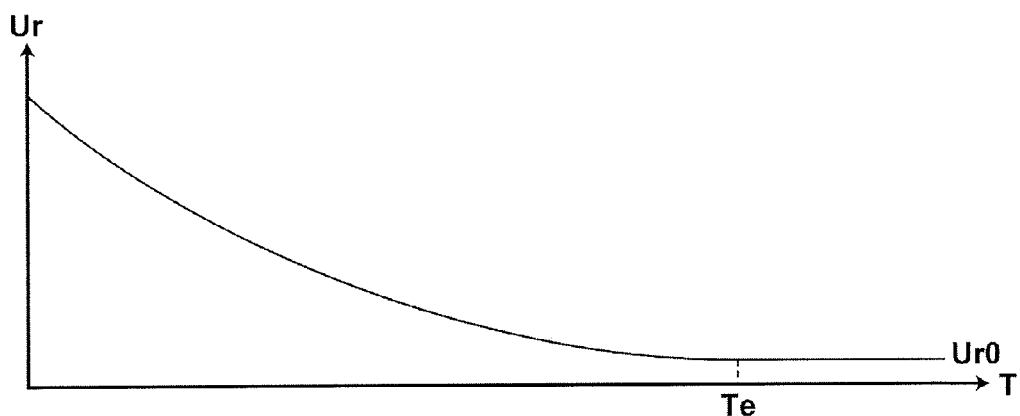
FIG. 6A shows an effect of the first embodiment of the invention.
Figure 6B:
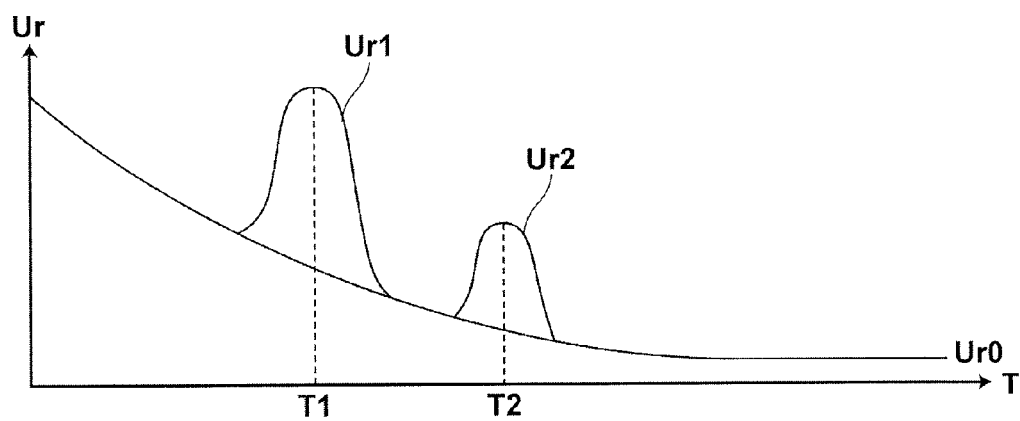
FIG. 6B shows the effect of the first embodiment of the invention.
Figure 6C:
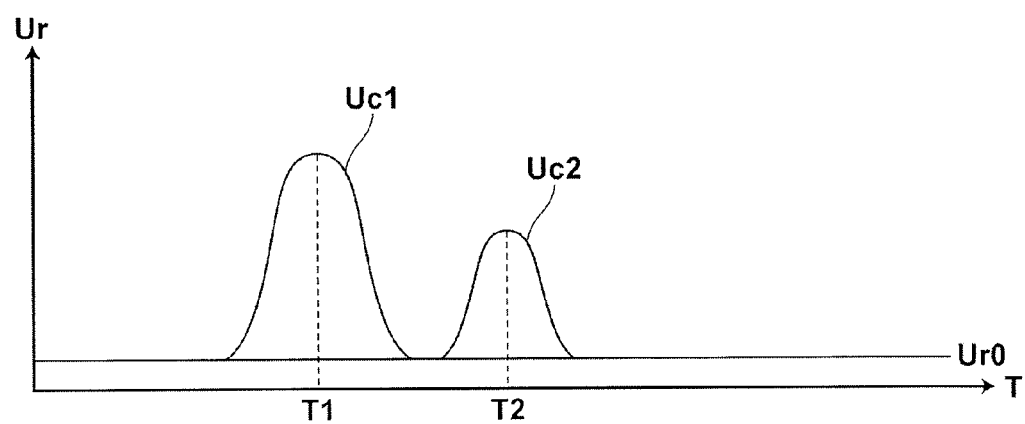
FIG. 6C shows the effect of the first embodiment of the invention.

FIGS. 6A to 6C show the effect of the first embodiment of the invention.

As shown in FIG. 6A, as the excitation light Le is applied to the equivalent microchip 11, the fluorescence Lk0 is emitted from the equivalent microchip 11 itself, and the fluorescence intensity Ur0 is detected. The fluorescence intensity Ur0 gradually attenuates, and sufficiently attenuates at a detection time Te. The temporal change during this attenuation is stored.

As shown in FIG. 6B, the excitation light Le is applied to the microchip 10 with the fluorescently-labeled biological sample R charged in the micro flow channel 12 thereof, and the biological sample R is electrophoresed to detect the fluorescence intensity. For example, the fluorescence intensity Ur0 of the fluorescence Lk0 emitted from the microchip 10 itself is detected, and then, the fluorescence intensities Ur1 and Ur2 from the components R1 and R2 in the biological sample R are detected at the detection times T1 and T2.

As shown in FIG. 6C, since the temporal change of the fluorescence intensity Ur0 from the equivalent microchip 11 for the period from the start of application of the excitation light to the detection time Te is stored, the fluorescence intensity Ur0 added to the fluorescence intensity Ur as the background is estimated.

Therefore, by carrying out the subtraction using the stored fluorescence intensity Ur0, the fluorescence intensity Uc with reduced influence of the background is detected with high accuracy in a shorter time. For example, fluorescence intensities Uc1 and Uc2 of the components R1 and R2 in the biological sample R are detected. Further, it is not necessary to apply any additional treatment to the microchip 10.

FIG. 7 is a flow chart according to a second embodiment of the invention.

The microchip 10 with the fluorescently-labeled biological sample R charged in the micro flow channel 12 thereof is prepared (ST2-1).

The microchip 10 is set on the confocal fluorescence microscope 200 to be ready for detecting the fluorescence intensity Ur (ST2-2).

The excitation light Le is applied to the microchip 10 with the fluorescently-labeled biological sample R charged in the micro flow channel 12 thereof, and the fluorescence intensity Ur0 of the fluorescence Lk0 emitted from the microchip 10 itself exposed to the excitation light Le is detected (ST2-3).

The fluorescence intensity Ur0 begins to attenuate and an initial temporal change of the fluorescence intensity Ur0 is detected. Based on the initial temporal change of the fluorescence intensity Ur0, the CPU 102 of the controlling section 100 estimates values of the temporal change of the fluorescence intensity Ur0 until it sufficiently attenuates (ST2-4). Specifically, in a case where the microchip made of PMMA is used in this embodiment, it is about 40 seconds from the start of application of the excitation light Le during which the fluorescence intensity Ur0 attenuates to about 70%, or desirably about 50 seconds from the start of application of the excitation light Le during which the fluorescence intensity Ur0 attenuates to about 60%. Specific example of the estimation method includes approximation by an exponential function, a power series, a logarithmic function or a fractional function. Approximation by an exponential function is desirable. Specific example of the estimation method further includes approximation achieved by preparing different types of microchips in advance, storing, for each microchip, a temporal change of the emitted fluorescence for the period from the start of application of the excitation light to the point at which the fluorescence intensity sufficiently attenuates, and selecting one of the stored temporal changes based on the initial temporal change of the fluorescence intensity Ur0.

The biological sample R is electrophoresed to be fed to the exposure area So (ST2-5). For example, the components R1 and R2 in the biological sample R are fed to the exposure area So.

The temporal change of the estimated fluorescence intensity Ur0 is subtracted from the detected fluorescence intensity Ur (ST2-6).

The fluorescence intensity Uc free of the influence of the fluorescence intensity Ur0 as the background is detected (ST2-7). For example, the fluorescence intensities Uc1 and Uc2 of the components R1 and R2 in the biological sample R are detected.

Figure 8A:
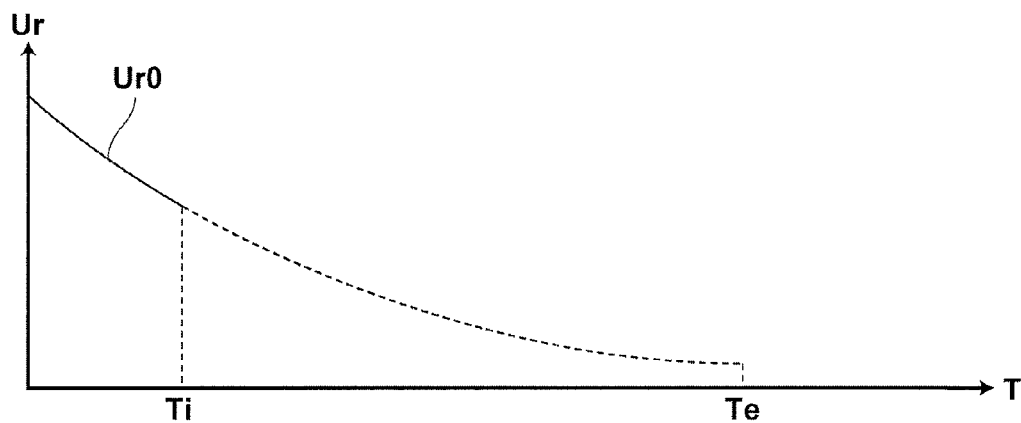
FIG. 8A shows an effect of the second embodiment of the invention.
Figure 8B:
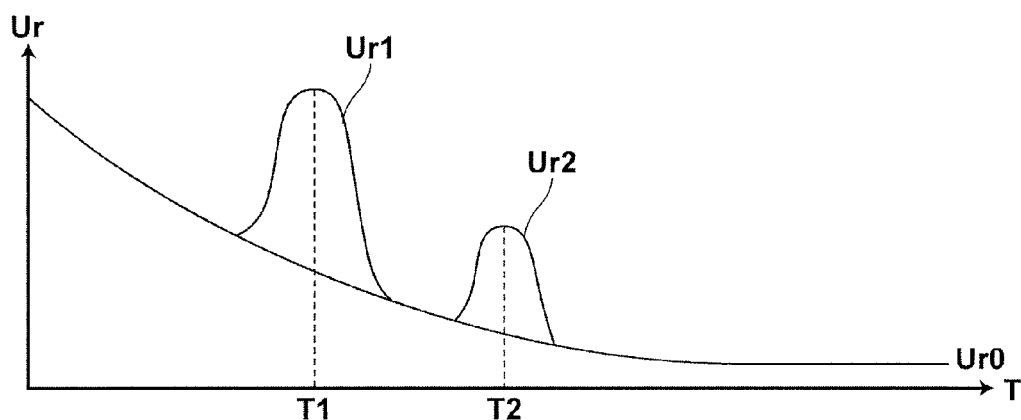
FIG. 8B shows the effect of the second embodiment of the invention.
Figure 8C:
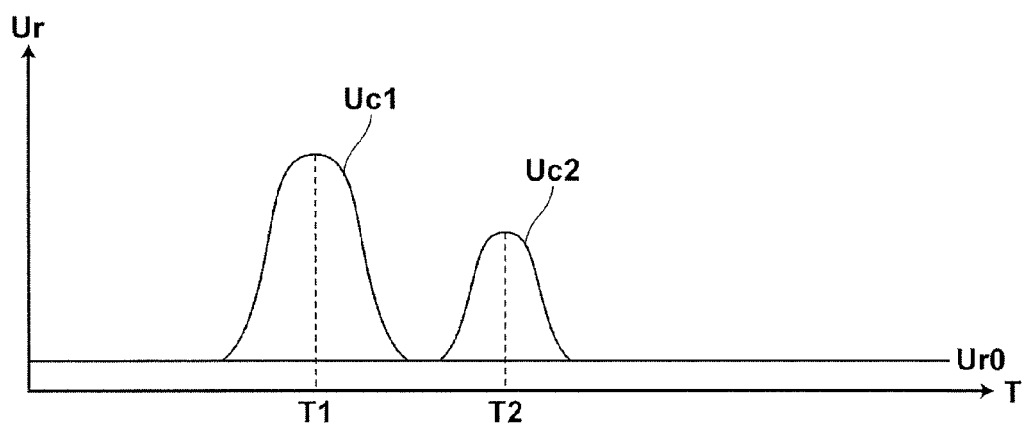
FIG. 8C shows the effect of the second embodiment of the invention.

FIGS. 8A-8C show the effect of the second embodiment of the invention.

As shown in FIG. 8A, as the excitation light Le is applied to the microchip 10 with the fluorescently-labeled biological sample R charged in the micro flow channel 12 thereof, the fluorescence Lk0 is emitted from the microchip 10 itself, and the fluorescence intensity Ur0 is detected. The fluorescence intensity Ur0 gradually attenuates. Based on the initial temporal change at the detection time Ti (the solid line in the drawing), the fluorescence intensity Ur until the detection time Te at which the fluorescence intensity of the fluorescence intensity Ur0 sufficiently attenuates is estimated (the dashed line in the drawing).

As shown in FIG. 8B, by electrophoresing the biological sample R, the fluorescence intensities Ur1, Ur2 of the components R1 and R2 in the biological sample R, for example, to which the fluorescence intensity Ur0 from the microchip 10 itself is added, are detected in turn.

As shown in FIG. 8C, since the temporal change of the fluorescence intensity Ur0 from the microchip 10 for the period from the start of application of the excitation light Le to the detection time Te is estimated, the fluorescence intensity Ur0 added to the fluorescence intensity Ur is estimated.

Therefore, by carrying out the subtraction using the estimated fluorescence intensity Ur0, the fluorescence intensity Uc with reduced influence of the background is detected with high accuracy in a shorter time. For example, the fluorescence intensities Uc1 and Uc2 of the components R1 and R2 in the biological sample R are detected. Further, it is not necessary to apply any additional treatment to the microchip 10.

The invention claimed is:

1. A fluorescence detection method for detecting a fluorescence intensity of fluorescence emitted when excitation light is applied to a microchip with a fluorescently-labeled biological sample fed thereto, the method comprising:
   detecting a fluorescence intensity of fluorescence emitted from an equivalent microchip itself for a period from the start of application of the excitation light until the fluorescence intensity sufficiently attenuates, the equivalent microchip being equivalent to the microchip;
   storing a temporal change of the detected fluorescence intensity;
   applying the excitation light to the microchip and feeding the biological sample to the microchip before a fluorescence intensity of fluorescence emitted from the microchip itself sufficiently attenuates;
   detecting the fluorescence intensity of the fluorescence emitted from the microchip for a period from the start of application of the excitation light to a point of time after the biological sample is fed to the microchip; and
   subtracting, from the fluorescence intensity detected from the microchip with the biological sample fed thereto, values of the stored temporal change of the fluorescence intensity of the fluorescence emitted from the equivalent microchip itself until the fluorescence intensity sufficiently attenuates, whereby detecting a fluorescence intensity of the fluorescence emitted from the biological sample exposed to the excitation light.

2. The fluorescence detection method as claimed in claim 1, wherein the steps of detecting the fluorescence intensity of fluorescence emitted from the equivalent microchip itself for the period from the start of application of the excitation light until the fluorescence intensity sufficiently attenuates and storing the temporal change of the detected fluorescence intensity are carried out for each of more than one microchips made of different materials to store different types of temporal changes, and the subtraction is carried out with selecting one of the different types of temporal changes to be used for the subtraction based on a material forming the microchip being used.

3. A fluorescence detection method for detecting a fluorescence intensity of fluorescence emitted when excitation light is applied to a microchip with a fluorescently-labeled biological sample fed thereto, the method comprising:
   applying the excitation light to the microchip and feeding the biological sample to the microchip before a fluorescence intensity of fluorescence emitted from the microchip itself sufficiently attenuates;
   detecting the fluorescence intensity of the fluorescence emitted from the microchip for a period from the start of application of the excitation light to a point of time after the biological sample is fed to the microchip;
   estimating a temporal change of the fluorescence intensity of the fluorescence emitted from the microchip for a period until the fluorescence intensity sufficiently attenuates, based on an initial temporal change of the fluorescence intensity of the fluorescence emitted from the microchip obtained through the detection; and
   subtracting, from the fluorescence intensity detected from the microchip with the biological sample fed thereto, values of the estimated temporal change of the fluorescence intensity of the fluorescence emitted from the microchip for the period until the fluorescence intensity sufficiently attenuates, whereby detecting a fluorescence intensity of the fluorescence emitted from the biological sample exposed to the excitation light.

4. The fluorescence detection method as claimed in claim 3, wherein the estimation of the temporal change is carried out by approximation by an exponential function based on the initial temporal change of the fluorescence intensity of the fluorescence emitted from the microchip.

5. The fluorescence detection method as claimed in claim 3, wherein the estimation of the temporal change is carried out by approximation by a power series based on the initial temporal change of the fluorescence intensity of the fluorescence emitted from the microchip.

6. The fluorescence detection method as claimed in claim 3, wherein the estimation of the temporal change is carried out by approximation by a logarithmic function based on the initial temporal change of the fluorescence intensity of the fluorescence emitted from the microchip.

7. The fluorescence detection method as claimed in claim 3, wherein the estimation of the temporal change is carried out by approximation by a fractional function based on the initial temporal change of the fluorescence intensity of the fluorescence emitted from the microchip.

8. The fluorescence detection method as claimed in claim 3, wherein the estimation of the temporal change is carried out by selecting one of different types of temporal changes based on the initial temporal change of the fluorescence intensity of the fluorescence emitted from the microchip, the different types of temporal changes being obtained by detecting a fluorescence intensity of fluorescence emitted from each of different types of microchips exposed to the excitation light for a period from the start of application of the excitation light until the fluorescence intensity sufficiently attenuates.

* * * * *